(12) United States Patent
Toivonen et al.

(10) Patent No.: US 6,463,170 B1
(45) Date of Patent: Oct. 8, 2002

(54) MONITORING SYSTEM FOR WEB BREAKS IN A PAPER MACHINE

(75) Inventors: Juha Toivonen, Jyväskylä; Jorma Snellman, Parviaisentie; Mika Valkonen, Terveyskatu, all of (FI)

(73) Assignee: Honeywell Oy (FI)

( * ) Notice: Subject to any disclaimer, the term of this patent is extended or adjusted under 35 U.S.C. 154(b) by 0 days.

(21) Appl. No.: 09/289,903

(22) Filed: Apr. 12, 1999

(30) Foreign Application Priority Data

Feb. 25, 1999 (FI) .................................................. 990408

(51) Int. Cl.$^7$ ................................................. G06K 9/00
(52) U.S. Cl. .......................... 382/141; 348/88; 356/430
(58) Field of Search .............................. 382/141, 148, 382/255, 181, 190, 216, 218, 254, 282, 305; 348/88, 86, 92, 240; 226/11, 17, 92; 356/430, 431, 429; 345/700

(56) References Cited

U.S. PATENT DOCUMENTS

| | | | |
|---|---|---|---|
| 4,716,978 A | * 1/1988 | Wales et al. | 177/25.12 |
| 5,113,454 A | 5/1992 | Marcantonio et al. | 382/50 |
| 5,301,866 A | * 4/1994 | Veh et al. | 226/11 |
| 5,305,099 A | * 4/1994 | Morcos | 348/88 |
| 5,307,970 A | * 5/1994 | Shibuya et al. | 226/92 |
| 5,440,648 A | * 8/1995 | Roberts et al. | 382/141 |
| 5,717,456 A | 2/1998 | Rudt et al. | 348/88 |
| 5,949,550 A | * 9/1999 | Arndt et al. | 356/430 |
| 6,084,681 A | * 7/2000 | Keane | 356/430 |
| 6,098,063 A | * 8/2000 | Xie et al. | 706/60 |
| 6,211,905 B1 | * 4/2001 | Rudt et al. | 348/88 |

FOREIGN PATENT DOCUMENTS

| | | |
|---|---|---|
| DE | 4133315 | 4/1992 |
| EP | 0037669 | 10/1981 |
| EP | 0046058 | 2/1982 |
| EP | 0366235 | 5/1990 |
| EP | 0543629 | 5/1993 |
| EP | 0566015 | 10/1993 |
| EP | 0837323 | 4/1998 |
| FI | 0980814 | 6/1999 |
| GB | 2248935 | 4/1992 |
| WO | 9808080 | 2/1998 |

\* cited by examiner

Primary Examiner—Leo Boudreau
Assistant Examiner—Kanji Patel
(74) Attorney, Agent, or Firm—Ostrolenk, Faber, Gerb & Soffen, LLP

(57) ABSTRACT

The invention relates to a monitoring system for web breaks in a paper machine. A web (W) is monitored by means of a number of cameras (1) and the image data of various camera positions is used for compiling focused image regions (12). Camera-specific image processing equipment (2, 12) is adapted to compile image change data by comparing the change between sequential images as far as the focused image region (12) is concerned. The image change data is compared with a normal level of image change and an alarm message (3a) is delivered if the image change level has a deviation from the reference level which exceeds a preset threshold value. A break alarm is set off, in case said alarm message (3a) is delivered by image change data comparators (3) of one or more pre-selected camera positions (P1–Pn).

17 Claims, 1 Drawing Sheet

MONITORING SYSTEM FOR WEB BREAKS IN A PAPER MACHINE

FIELD OF THE INVENTION

The present invention relates to a monitoring system for web breaks in a paper machine.
- a number of cameras for imaging various positions of a monitored web;
- digital image processing equipment for storing image data from a plurality of camera positions; and
- selection means for choosing a focused picture region from the image data of various camera positions.

A monitoring system including cameras which image various positions of a monitored web, has been used earlier only for a subsequent analysis of web breaks. However, such a system has not been employed as an actual break sensor capable of detecting a web break. Typically this system has been used in conjunction with traditional break sensors used in a paper machine which are often unreliable, and in certain positions, such as at the wet end of a machine, these traditional sensors have been found generally completely useless.

This type of monitoring systems have been used earlier for a subsequent analysis of web breaks, but such systems have not been employed as an actual break sensor capable of detecting a web break. Traditional break sensors used in a paper machine are often unreliable and such traditional sensors are generally completely useless in certain positions, particularly at the wet end of a machine.

SUMMARY OF THE INVENTION

An object of the invention is to develop further a monitoring system of the above-described type to enable its use in lieu of traditional break sensors both in web break monitoring systems and in the actual control of a paper machine.

This object is achieved on a monitoring system for web breaks in a paper machine. A web is monitored by means of a number of cameras and the image data of various camera positions is used for compiling focused image regions. Camera-specific image processing equipment is adapted to compile image change data by comparing the changes between sequential images as far as the focused image region is concerned. The image change data is compared with a normal level of image change and an alarm message is delivered if the image change level has a deviation from the reference level which exceeds a preset threshold value. A break alarm is set off, in case the alarm message is delivered by image change data comparators of one or more pre-selected camera positions.

This object is achieved on the basis of the characterizing features set forth in the annexed claim 1. The non-independent claims disclose preferred embodiments of the invention.

BRIEF DESCRIPTION OF THE DRAWINGS

The invention will now be described in mere detail by way of an exemplay embodiment with reference made to the accompanying drawing FIG. 1, which depicts one preferred embodiment of the invention in a block diagram.

DETAILED DESCRIPTION

Figure 1:
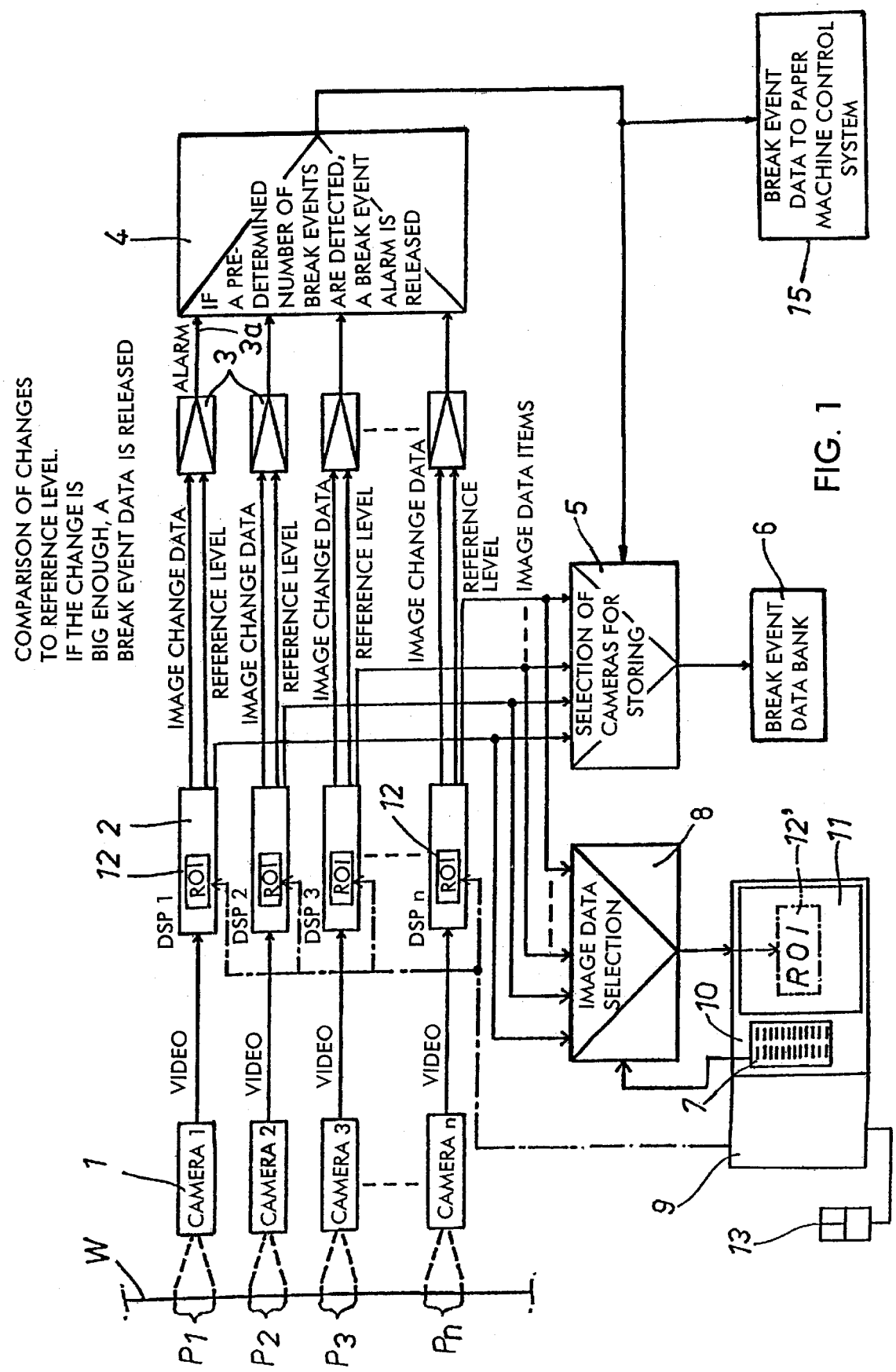

The source of image in the block diagram comprises a number of video cameras, which produce continuously a video image of a monitored paper web W from its various image positions P1 . . . Pn. These positions have been selected W from its various image positions P1 . . . Pn. These positions have been selected from among the locations that are critical in terms of web breaks. A system of the invention can be included in a larger system, wherein some of the cameras operate in other monitoring functions, as described in the Applicant's co-pending patent applications FI-981736 which corresponds to U.S. application Ser. No. 09/372,001 and FI-990120.

The image information received from each camera is processed in a digital signal processor 2 or a DSP-processor. The signal processors resemble ordinary microprocessors, yet contain e.g. the use of floating point number technology and address formats for easier addressing. In addition, the DSP differs remarkably from an ordinary processor in terms of its architecture, having been designed for functions which involve lots of data, and multiplications with integers and transmissions of data are statistically significant operations. The DSP-processors enable the implementation of several different and simultaneous calculation routines associated with image analyzing, the results of which can be applied to automatically perceiving the changes appearing in image information.

The present invention is partly constituted by tools made available for a user, whereby the user can focus on a region or frame, which is optional in terms of its location and size, from the picture area of each camera. In reference to the DSP-processors 2, this focused frame is indicated by a reference numeral 12 (ROI/Region Of Interest). The selection of a size and a location for the focused frame 12 can be controlled by means of tools 7, 8, 10–13 included in a user's computer 9. Selection icons 7 visible on a monitor 10 can be used by the user by pointing with a mouse 13 in order to choose an image 11 of a desired camera position to be displayed. In other words, the images of all camera positions are received in the user's computer 9, but the image data selection unit 8 is used for choosing the image 11 of any given camera position to be shown on the screen 10, wherein a focused frame or region 12' is defined in terms of its size and location in accordance with the user's selection. Naturally, the selection is focused on that region of the image 11 in which a web break is expected to cause most perceptible image changes. The delimitation corresponding to the focused region 12' in the image 11 of any selected camera position can be assigned by way of the computer 9 to the DSP-processor 2 of a corresponding camera position. Hence, the control supplied by the user's computer 9 is applied to the digital image processing equipment 2 for a video image received from the cameras 1, said equipment operating on a fifo-principle and the temporal duration of image data stored therein being variable from a few seconds to several minutes. Thus, the image data stored from each camera position may contain a few dozen or even several hundred sequential images 11 and, respectively, focused frames or regions 12/12' included therein.

The digital image processing equipment 2 is adapted to compile image change data by comparing the change between sequential images as far as a focused image region or frame is concerned. Furthermore, the digital image processing equipment 2 is adapted to provide a reference level for the image change, which represents a normal level of image change data. The reference level can be established in a plurality of ways and it can be based e.g. on one or more of the following actions:
- performing an automatic image analysis continuously or periodically for determining a normal image change level the user selects a reference level or a parameter relevant thereto while selecting or changing of the image region 12, 12' producing the image change data using image change data, which dates further back than the actual, real-time image change data, as a reference level or as one parameter in establishing a reference level.

From each DSP-processor 2 the image change data and the reference level are carried to camera-specific comparators 3, which compare the image change data to the reference level and produce an alarm message 3a in case the deviation of the image change data from the reference level exceeds a preset threshold value. The alarm limits, i.e. the maximum acceptable deviations of image change data from a reference level, are thus predetermined with settings established by a user, principally by means of empirical knowledge, said knowledge accumulating along with working experiences. It is obvious that various camera positions have dissimilar optimal alarm limits in view of optimizing the relationship between sensitivity and false alarms. A major factor in this optimization is a solution of the invention, wherein the image change data is only compiled from the picture region 12 focused on an object of interest.

From the comparators 3 the alarm messages 3a are carried to an alarm device 4, which produces an actual break alarm if an alarm message 3a is emitted by the image change data comparators 3 of one or more pre-selected camera positions P1–Pn. Selection means 5 can be used for choosing the cameras whose image data will be stored in a break data bank 6. In addition, a message received from the device 4 may contain information as to which camera positions have set off an alarm. This can be used as a directive for the storage selection means 5 for storing the image data of relevant camera positions in the break data bank 6.

If an alarm is based on the image position of a single camera, it is possible to aim for the elimination of false alarms by using a suitable hysteresis. However, an absolutely positive indication of a break is obtained by using a combination of several cameras, whereby the break message must be received from a number of cameras (and, respectively, it is necessary to receive a number of alarm messages 3a) before it results in an actual break alarm from the alarm device 4.

Hence, the web break monitoring system of the invention can be used for effecting the storage of a break incident by means of just selected, desired camera positions P1–Pn.

Reference numeral 15 designates a paper machine control system, which is also supplied with a break message delivered by a monitoring system of the invention.

Unlike the depicted block diagram, it is possible that the focused image region 12 is already selected with a camera 1. This can be done either with selection means included in the camera itself or under the control of the user's computer 9.

Furthermore, unlike the block diagram, it is possible to operate the user's computer 9, if this is desirable, also for driving the storage selection means 5 in such a manner that the selection of a user also increases or reduces the number of those cameras 1 whose image data is stored in the break data bank 6 in connection with a break alarm. In addition, the user computer 9 may be in communication with the break data bank 6 for displaying the images stored therein on the monitor 10 for analysis.

What is claimed is:

1. A monitoring system for web breaks in a paper machine, comprising:

a number of cameras for imaging various positions of a monitored web;

digital image processing equipment for storing image data from a plurality of camera positions; and a selector for choosing a focused picture region from said image data of a selectable individual picture of various camera positions, said digital image processing equipment is adapted to compile image change data by comparing the change between sequential images as far as said focused image region is concerned, and a reference level for said image change data, which represents a normal level of said image change data;

comparators for comparing said image change data to said reference level and for setting off an alarm message, in case said image change data has a deviation from said reference level which exceeds a preset threshold value; and an alarm equipment for setting off a break alarm if said alarm message is delivered said image change data comparators of one or more camera positions.

2. A monitoring system as set forth in claim 1, further comprising a storage selector, which under the control of the alarm equipment for choosing those cameras which correspond to positions whose image data is stored in a break data bank in connection with a break alarm.

3. A monitoring system as set forth in claim 1 wherein the alarm equipment is adapted not to set off an alarm until the image change data deviation from the reference level in the focused image region for a number of positions exceeds said threshold value.

4. A monitoring system as set forth in claim 1, wherein the reference level is based on one or more of the following actions:

an automatic image analysis continuously or periodically for determining a normal image change level;

a user's selection in connection with the selection or change of an image region producing the image change data;

the use of image change data, which dates further back than the actual, real-time image change data, as a reference level or as one parameter in establishing a reference level.

5. A monitoring system as set forth in claim 1, wherein the selection function for framing the focused image region relevant to the image change data, i.e., the selection of a size and location for the focused image region, is controllable by means of tools included in a user's computer and the control is applied to said digital image processing equipment.

6. A monitoring system as set forth in claim 2, wherein the alarm equipment is adapted not to set off an alarm until the image change data deviation from the reference level in a focused image region for a number of positions exceeds said threshold value.

7. A monitoring system as set forth in claim 2, wherein the reference level is based on one or more of the following actions:

an automatic image analysis continuously or periodically for determining a normal image change level, a user's selection in connection with the selection or change of an image region producing the image change data, the use of image change data, which dates further back than the actual, real-time image change data, as a reference level or as one parameter in establishing a reference level.

8. A monitoring system as set forth in claim 3, wherein the reference level is based on one or more of the following actions:

an automatic image analysis continuously or periodically for determining a normal image change level, a user's selection in connection with the selection or change of an image region producing the image change data, the use of image change data, which dates further back than the actual, real-time image change data, as a reference level or as one parameter in establishing a reference level.

9. A monitoring system as set forth in claim 6, wherein the reference level is based on one or more of the following actions:

an automatic image analysis continuously or periodically for determining a normal image change level a user's selection in connection with the selection or change of an image region producing the image change data the use of image change data, which dates further back than the actual, real-time image change data, as a reference level or as one parameter in establishing a reference level.

10. A monitoring system as set forth in claim 2, wherein the selection function for framing the focused image region relevant to the image change data, i.e. the selection of a size and location for the focused image region, is controllable by means of tools included in a user's computer and the control is applied to said digital image processing equipment.

11. A monitoring system as set forth in claim 3, wherein the selection function for framing the focused image region relevant to the image change data, i.e. the selection of a size and location for the focused image region, is controllable by means of tools included in a user's computer and the control is applied to said digital image processing equipment.

12. A monitoring system as set forth in claim 6, wherein the selection function for framing the focused image region relevant to the image change data, i.e. the selection of a size and location for the focused image region, is controllable by means of tools included in a user's computer and the control is applied to said digital image processing equipment.

13. A monitoring system as set forth in claim 4, wherein the selection function for framing the focused image region relevant to the image change data, i.e. the selection of a size and location for the focused image region, is controllable by means of tools included in a user's computer and the control is applied to said digital image processing equipment.

14. A monitoring system as set forth in claim 7, wherein the selection function for framing the focused image region relevant to the image change data, i.e. the selection of a size and location for the focused image region, is controllable by means of tools included in a user's computer and the control is applied to said digital image processing equipment.

15. A monitoring system as set forth in claim 8, wherein the selection function for framing the focused image region relevant to the image change data, i.e. the selection of a size and location for the focused image region, is controllable by means of tools included in a user's computer and the control is applied to said digital image processing equipment.

16. A monitoring system as set forth in claim 9, wherein the selection function for framing the focused image region relevant to the image change data, i.e. the selection of a size and location for the focused image region, is controllable by means of tools included in a user's computer and the control is applied to said digital image processing equipment.

17. A monitoring system for web breaks in a paper machine, comprising:

a number of cameras operative to produce pictures of a monitored web at a corresponding number of locations;

digital image processing equipment in communication with the number of cameras and operative to store image data of each of said pictures from said number of cameras;

a selector operative to select and image a focused picture region from said image data of a selectable picture;

said digital image processing equipment being operative to compile image change data by comparing sequential images of said focused picture region; and a reference level for said image change data, which represents a normal level of said image change data;

at least one comparator operative to compare said image change data to said reference level and to set off an alarm message, in case said image change data has a deviation from said reference level which exceeds a preset threshold value; and an alarm equipment operative to set off a break alarm if said alarm message has been set off by the at least one comparator.

* * * * *